United States Patent
Austin et al.

[11] Patent Number: 5,884,693
[45] Date of Patent: Mar. 23, 1999

[54] INTEGRAL HEAT PIPE ENCLOSURE

[75] Inventors: Thomas A. Austin; Stephen Greer, both of Santa Rosa, Calif.; Andrew Low, McKinney, Tex.

[73] Assignee: DSC Telecom L.P., Plano, Tex.

[21] Appl. No.: 1,624

[22] Filed: Dec. 31, 1997

[51] Int. Cl.[6] .................................................. F28D 15/00
[52] U.S. Cl. ................ 165/104.33; 165/45; 165/104.33; 165/104.22; 257/715; 361/724
[58] Field of Search ......................... 165/104.26, 104.22, 165/104.33, 104.14, 104.23, 104.24, 45; 361/700, 724; 257/715

[56] References Cited

U.S. PATENT DOCUMENTS

| | | | |
|---|---|---|---|
| 3,024,298 | 3/1962 | Goltsos et al. | 174/15 |
| 3,461,952 | 8/1969 | Decker et al. | 165/104.33 X |
| 4,009,417 | 2/1977 | Waldon et al. | 361/38 |
| 4,009,418 | 2/1977 | Bennett | 361/38 |
| 4,049,407 | 9/1977 | Bottum | 62/2 |
| 4,306,613 | 12/1981 | Christopher | 165/32 |
| 4,449,579 | 5/1984 | Miyazaki et al. | 165/104.33 |
| 4,600,050 | 7/1986 | Noren | 165/104.14 |
| 4,685,512 | 8/1987 | Edelstein et al. | 165/104.14 |
| 4,790,370 | 12/1988 | Niggemann | 165/104.33 |
| 4,921,039 | 5/1990 | Ghiraldi | 165/104.33 X |
| 4,921,043 | 5/1990 | Ghiraldi | 165/104.33 X |
| 4,949,164 | 8/1990 | Ohashi et al. | 761/700 X |
| 5,579,830 | 12/1996 | Giammaruti | 165/104.27 |

FOREIGN PATENT DOCUMENTS 0255849   12/1926   United Kingdom .............. 165/104.33

OTHER PUBLICATIONS

IBM Technical Disclosure Bulletin, p. 2532, N.G. Aakalu et al., Integrated Cooling for High–Density Electronic Components, Jan. 1972.

*Primary Examiner*—Ira S. Lazarus
*Assistant Examiner*—Christopher Atkinson
*Attorney, Agent, or Firm*—Fliesler, Dubb, Meyer & Lovejoy LLP

[57] ABSTRACT

A passive cooling system for cooling an enclosure containing electronic components. A hollowed portion of the enclosure is formed as an integral heat pipe containing a working fluid. The hollowed portion has an evaporator section located at the top and a condenser section located at the bottom. The enclosure also has hollowed side walls which serve as passage ways for the working fluid to flow through in between the evaporator and condenser sections. Gravity and the pressure of evaporation force the working fluid down to the condenser section. A wick is provided for returning the working fluid to the evaporator section by capillary action. Additionally, an ultrasonic transducer driven by the heat rejected from the condenser section may be used to help return the working fluid to the evaporator section. Finally, a check valve may be employed before the evaporator section for the working fluid to flow through.

18 Claims, 3 Drawing Sheets

INTEGRAL HEAT PIPE ENCLOSURE

BACKGROUND OF THE INVENTION

1. Field of the Invention:

The present invention is directed toward the field of cooling systems and more particularly to a passive means of cooling an enclosure containing electronics by providing an enclosure having an integral heat pipe incorporated into the enclosure.

2. Art Background:

It is common to those skilled in the art to house electronics, such as telecommunications, cable television and traffic light control equipment, in enclosures to protect them from contaminants in the surrounding environments, and to shield them from electromagnetic radiation. It is also well known that these electronics generate significant heat during operation, and this heat must be dissipated to prevent damage or destruction to the electronics. The dissipation of heat will ensure that the electronics operate only within a limited temperature range.

In the past, cooling of electronics was achieved by flowing a cooling fluid over and/or around the heat source. Once heated by the heat source, the cooling fluid was vented from the enclosure to conduct file heat away from the enclosure. One method used for cooling was heat exchangers which separately transferred heat from the enclosed heat source to an outside cooling medium. However, this presented a problem because the enclosure or electronics did not remain isolated from the outside environment and were susceptible to contaminants. Furthermore, to operate effectively, these types of heat exchangers required the use of one or more fans to force air across their surfaces. Or, in systems requiring extreme heat dissipation, a traditional refrigeration cycle was required. The fan or refrigeration cycle methods both required an additional power source along with moving parts and motors for operation. Since in some cases power was not available or access to the moving parts was difficult because the electronics were located in a remote location, methods as described above were not generally practical.

Furthermore, many prior art devices have completely buried the electronics underground. Burying the electronics made access to the electronics very difficult for repair and maintenance purposes. Moreover, wholes dug in the ground to receive the enclosures were irregular in shape, thereby creating air pockets between the enclosure and the surrounding soil. These air pockets made it difficult to transfer any considerable amount of heat generated by electronic components to the surrounding soil. As a result of these problems, it has been discovered that more efficient cooling of electronics can be obtained through the use of passive heat pipes which require no external power source and contain no moving parts.

Generally, the heat pipe is in the form a vacuum-tight vessel in a particular geometric shape which is evacuated and partially filled with a working fluid. The heat pipe passively transfers heat from a heat source to a heat sink where heat is dissipated. As the heat is conducted into the heat pipe, the fluid is vaporized in an evaporator section creating a pressure gradient in the heat pipe. This forces the vapor to flow along the heat pipe to the condenser section, where the vaporized fluid is condensed and turned back to its fluid state by giving up its latent heat of vaporization. The working fluid is then returned to the evaporator section to repeat the process of removing the heat generated by the heat source.

One method used to achieve cooling by use of a heat pipe places the evaporator section at the lower end and the condenser section at the upper end where the heat pipe is in a substantially vertical position. Once the working fluid has been condensed, the liquid flows by gravity back to the evaporator section. Although no wicking structure is needed to return the working fluid to the evaporator section, this method is less efficient than the present invention wherein the evaporator section is located at the top of the enclosure because heat naturally migrates in an upward direction. Furthermore, when the condenser section is placed at the upper end, the system is less efficient because the temperature of the ground is lower than the temperature of the outside environment. Placing the condenser section at the lower end serves as a more effective way of dissipating heat.

SUMMARY OF THE INVENTION

It is therefore, an advantage of this invention to provide a passive cooling system which functions efficiently, effectively and has no moving mechanical parts which require routine maintenance and repair.

Another advantage of this invention is to provide a passive cooling system which utilizes heat pipe principles in a simple structure.

Another advantage of this invention is to provide an enclosure where the heat pipe used for cooling is an integral part of the enclosure itself.

A further advantage of this invention is to provide a cooling system which does not require an outside power source and therefore is inexpensive in operation and manufacture.

Yet another advantage of this invention is to provide a cooling system which allows the electronics to avoid contact with the outside environment thereby achieving a contaminant free system.

A still further advantage of this invention is to provide a more efficient cooling system by placing the evaporator at the top of the enclosure since heat rises by natural convection.

Yet another advantage of this invention is to provide a cooling system which is more efficient overall by placing the condenser section at the bottom of the enclosure since the ground has a lower temperature relative to the temperature of the outside environment and can dissipate more heat. These and other advantages of the invention will become obvious upon further investigation.

In accordance with the present invention, a new and improved passive cooling system for cooling an enclosure containing electronic components is provided. A portion of the enclosure is formed as an integral heat pipe and a working fluid is contained within. The enclosure has an evaporator section located at the top and a condenser section located at the bottom. The enclosure also has hollowed side walls which serve as passage ways for the working fluid to flow through between the evaporator and condenser sections for the liquid-to-vapor phase change upon absorption of heat dissipated from the electronics and a vapor-to-liquid phase change after condensation has occurred in the system. After the working fluid is vaporized by the evaporator section, it flows to the condenser section by gravity and the pressure of evaporation. Also, a solar load, which could include heat input from the sun, may exist to aid in the vaporization of the working fluid. Once the working fluid is condensed, it is returned to the evaporator section by a capillary action which is obtained by wicking. A loop heat pipe may be used because it is more efficient than a conventional heat pipe in pumping upward against gravity. Additionally, an ultrasonic generator or transducer driven by the heat rejected from the condenser section may be used to help return the working fluid to the evaporator section. Finally, a check valve may be employed before the evaporator section for the fluid to flow through. This will prevent reverse flow and make sure the working fluid flows in one direction.

BRIEF DESCRIPTION OF THE DRAWINGS

The above and other advantages of the present invention will be apparent upon consideration of the following detailed description, taken in conjunction with the accompanying drawings, in which like reference characters refer to like parts throughout, and in which.

DETAILED DESCRIPTION

The present invention in general relates to passive cooling systems. While a preferred embodiment relates to an enclosure for housing telecommunication electronics, it is understood that the present invention may be used to cool various other electronic systems. Moreover, although a preferred embodiment of the present invention works with the enclosure partially immersed in the ground, which acts as a heat sink to cool the working fluid, it is understood that the enclosure according to the present invention may be situated in various other locations, utilizing other forms of heat sinks, in alternate embodiments.

Figure 1:
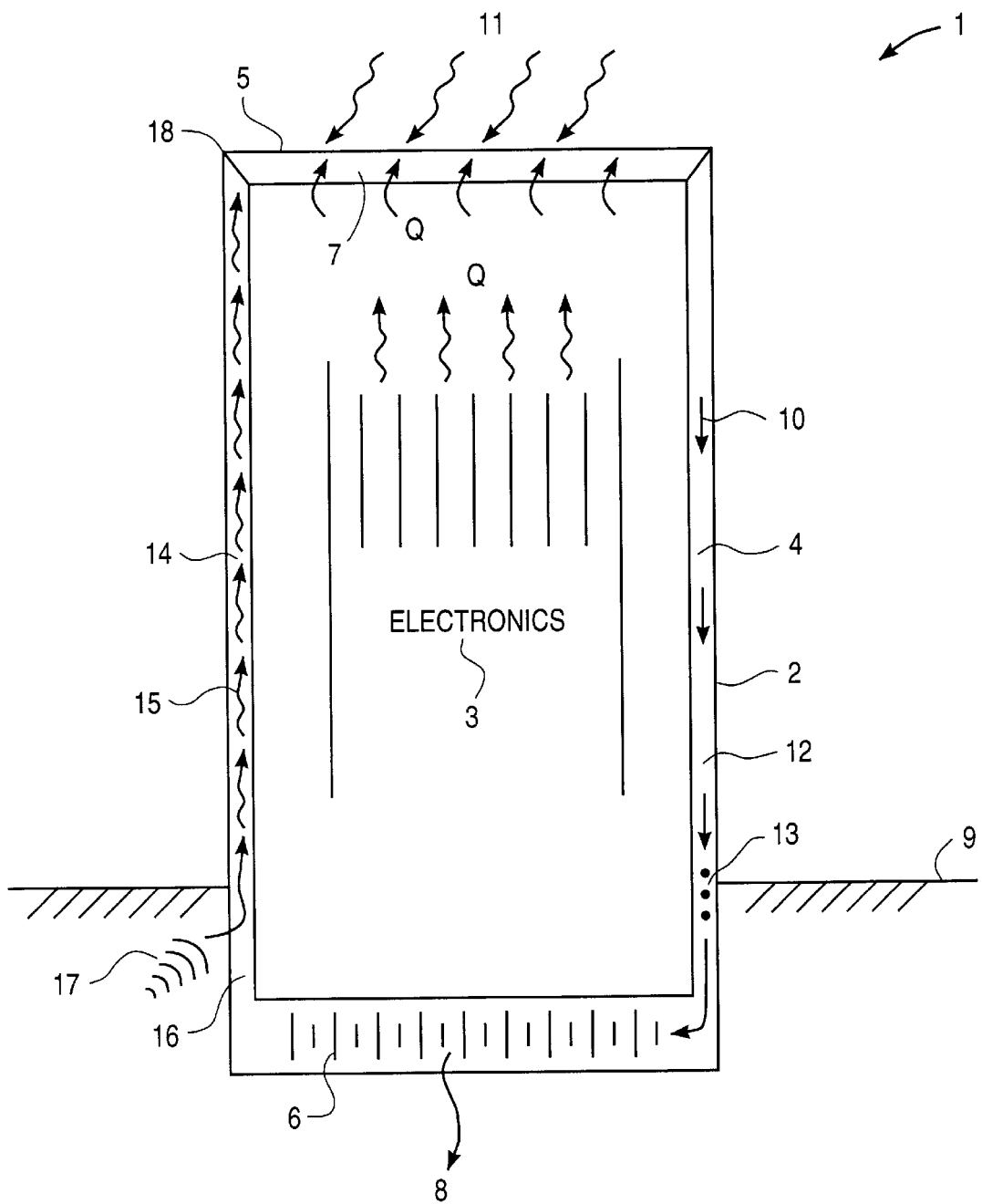
FIG. 1 is a cross-sectional view of the passive cooling system of the present invention.

Referring to the drawings, FIG. 1 depicts a passive cooling system 1. The system 1 cools heat generating components 3 via the incorporation of a heat pipe into a pedestal enclosure 2. As can be seen from FIG. 1, the enclosure 2 has mounted within it heat generating components 3 and provides a means for protecting the components from contaminants. The enclosure preferably comprises a cabinet design with an hinged door which allows for access to the components (not shown). The walls of the enclosure include a portion 4 which is hollow and forms an integral heat pipe. The material of the integral heat pipe may be for example, copper, gold, or aluminum. The preferred and most common material of the integral heat pipe is copper. Gold is the most efficient material but the cost of gold prohibits the use of it. Aluminum may be a preferable material to copper and gold for cost reasons but is the least efficient. The hollowed portion has a top section 5 and a bottom section 6. The top section 5 forms the evaporator section of the integral heat pipe enclosure and provides a means for turning the fluid to vapor form. The bottom section 6 forms the condenser section of the integral heat pipe enclosure and provides a means for returning the fluid to liquid form. The condenser section 8 is in thermal exchange with the ground 9. The hollowed portion 4 of FIG. 1 is shown as containing a working fluid 10 which is a refrigerant and may be for example, Freon, ammonia, water, methanol or some other refrigerant. The latent heat of absorption of Freon in a changing phase is considerably more efficient than water when being used in a passive cooling system. Ammonia is even more efficient that Freon and has about three times as much heat absorption capacity of an equal volume of Freon.

As will be understood from the previous discussion, as the heat generating components 3 in the enclosure operate, the heat within the enclosure rises to the evaporator section 7 which causes the working fluid 10 to vaporize. As the fluid vaporizes in the evaporator section, it is forced to the parallel condenser section 8 as a result of the force of gravity and the pressure of the evaporation. Additionally, a solar load 11 shown in FIG. 1 may exist at the top 5 of the hollowed portion dependent upon the location of the enclosure and weather conditions. A solar load 11 helps to ensure efficient and effective vaporization of the fluid 10. Once the vaporized working fluid reaches the bottom 6 of the hollowed portion through a side passageway 12, it passes through the condenser section 8 of the hollowed portion. The vaporized working fluid 13 will condense once the heat generated from the heat generating components is transferred to a heat sink 9, and then the fluid returns to the evaporator section 7 through the other side passageway 16 of the hollowed portion. As is shown in FIG. 1, the liquid working fluid 14 is returned to the evaporator section 7 by wicking 15 and/or an ultrasonic transducer 17. A wick 15 is positioned in the hollowed side passageway 16 of the enclosure 2. The wick can be fabricated out of any suitable thin heat pipe wicking material, but the wick is preferably formed of a fine meshed network type material having very small pores or openings, such as stainless steel. The liquid working fluid is absorbed by the porous wick so that the fluid moves up by a capillary pumping action toward the evaporator section. The capillary action is allowed by the narrow channels in the side passageway 16. Also, an ultrasonic transducer 17 may be used for increased capillary pumping to help return the working fluid to the evaporator section 7. The ultrasonic transducer 17 can be driven by the heat rejected from the condenser section 8. The ultrasonic transducer 17 functions as a thermoelectric device and operates under a principle known as the Seebeck Effect. The Seebeck Effect is known as the creation of a current when two different conducting materials are joined in a loop such that the two junctions are maintained at different temperatures. The temperature difference is usually maintained by application of heat to one end of the junction, thus causing an induced voltage. This will eliminate the need of a separate power source for driving the ultrasonic transducer. Before the liquid working fluid reaches the evaporator section, it must pass through a check valve 18 which prevents reverse flow of the liquid working fluid and assures flow in one direction.

This process will continuously repeat as long as the heat generated from the heat generating components and transferred to the evaporator section is greater than the temperature of the condenser section. If the condenser section/ ambient temperature reaches a higher temperature, then the process will discontinue because the system will have reached equilibrium. Theoretically, reaching a system equilibrium is possible, but the process in the present invention will continuously repeat because the ground performs as an infinite heat sink and will not rise to the temperature of the outside environment at the depth in which the condenser is buried. As a result of the infinite heat sink, the condenser section will remain at a lower temperature.

Figure 2:
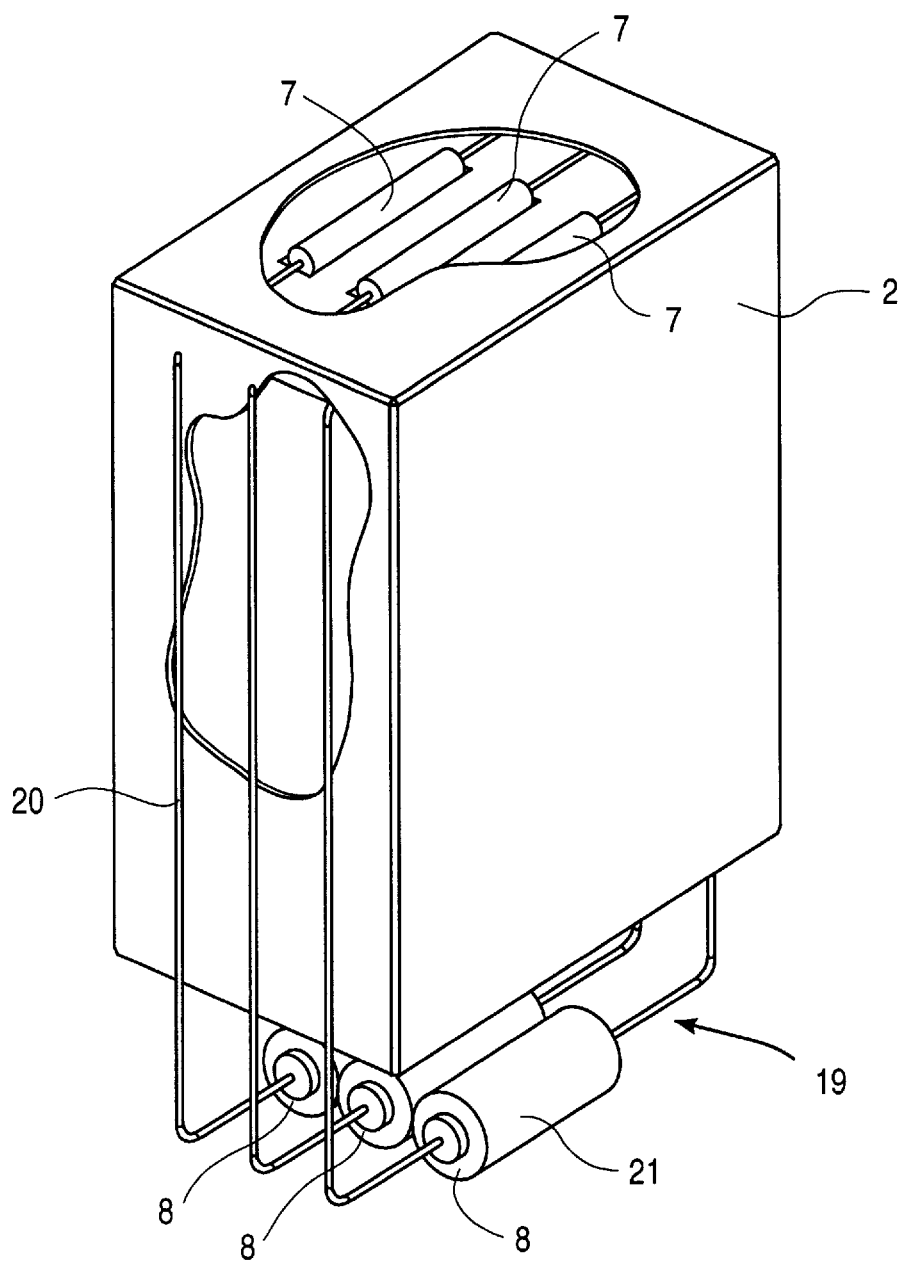
FIG. 2 is a perspective view of the passive cooling system of the present invention utilizing a loop heat pipe.

With reference now to FIG. 2, this is a preferred embodiment of the passive cooling system where the heat pipe principles used involve loop heat pipes 19 embedded in the enclosure 2. Loop heat pipes are more efficient than conventional heat pipes in situations where the evaporator section is above the condenser section because the liquid flow path through the capillary wick structure is much shorter in a loop heat, thus limiting liquid flow losses due to high gravitational limitations. Preferably, the enclosure shown in FIG. 2 uses three loop heat pipes 19, although the enclosure is not limited to the use of three loop heat pipes.

Figure 3:
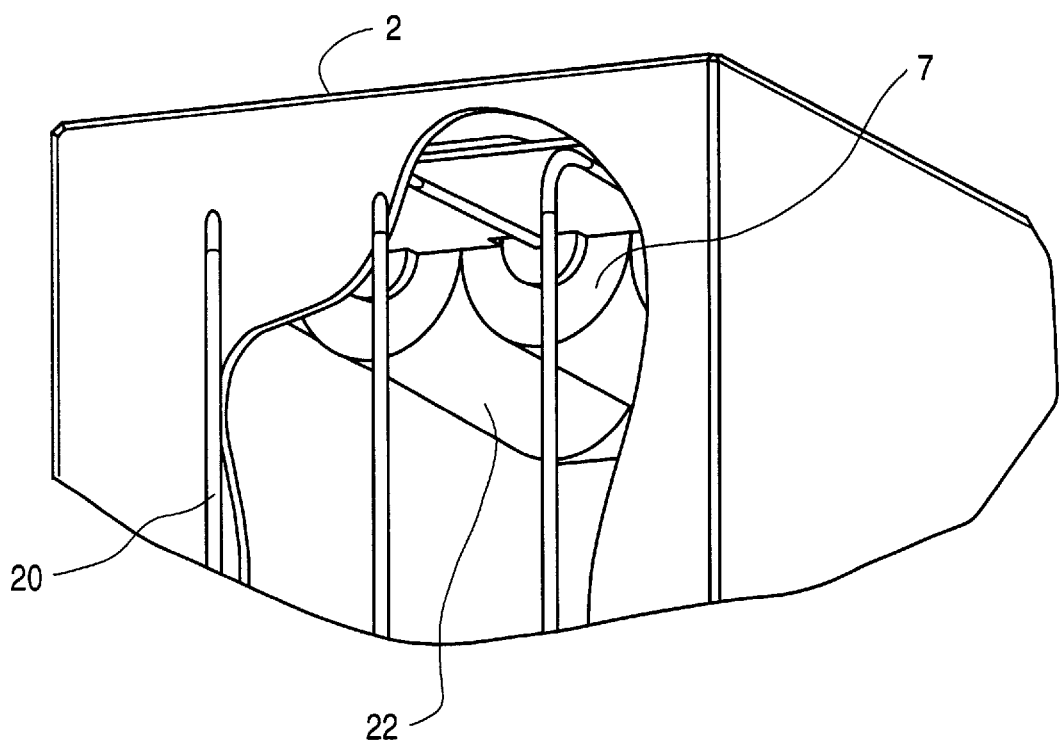
FIG. 3 is a partial sectional view showing the details of the evaporator section of the present invention.

The hollowed portion in the walls of the enclosure has an evaporation section 7 where three elongated cylindrical evaporators 7 are located, and a condenser section 8 where three elongated cylindrical condensers 8 are embedded in the ground. The evaporators 7 are connected to the condensers 8 by conduits 20 which are embedded in the side passageways 12, 16 in the walls of the enclosure. With reference to the condensers 8, the ground 9 serves as the actual heat sink in thermal exchange with the condensers which comprise thin-walled plastic tubes 21 embedded in the ground. To increase the efficiency and effectiveness of the thermal exchange to the ground, the condensers may be buried in grout which is a concrete mixture (not shown), preferably two to four feet below ground surface. A grout mixture used in combination with the ground soil will eliminate the irregularities in the ground due to air pockets which are created when the surrounding soil is removed and replaced. Additionally, fins 22 shown in FIG. 3, may be used to increase the effective heat transfer surface area of the evaporator section 7. Furthermore, the condenser section 8 may utilize fins (not shown). This will increase the rate of thermal dissipation of heat energy into and out of the liquid working fluid 14. However, the fins 22, although advantageous, are not an essential feature of the present invention.

The advantages of the passive cooling system 1 as described above include the fact that there are no moving parts requiring maintenance and that the heat pipe is an integral part of the enclosure. Also, since it is a passive system, there is no power source needed and the system may be utilized in remote locations where a power source may be difficult to provide. Finally, because the evaporator section is located at the top of the enclosure, the system is more effective and efficient since heat rises by natural convection.

Although the present invention has been described in terms of specific exemplary embodiments, it will be appreciated that various modifications and alterations might be made by those skilled in the art without departing from the spirit and scope of the invention.

What is claimed is:

1. A passive cooling system for cooling heat generating components comprising:
   (a) an enclosure having heat generating components mounted within;
   (b) a hollowed portion of said enclosure forming an integral heat pipe;
   (c) a working fluid contained within said hollowed portion;
   (d) an evaporator section at a top of said hollowed portion;
   (e) a condenser section at a bottom of said hollowed portion; and
   (f) said hollowed portion having first and second side passageways.

2. A passive cooling system as claimed in claim 1, wherein said working fluid contained within said evaporator section vaporizes and creates a vapor working fluid upon an absorption of heat generated from said heat generating components.

3. A passive cooling system as claimed in claim 2, wherein said vapor working fluid flows down through said first side passageway to said condenser section by gravity and a pressure created by evaporation.

4. A passive cooling system as claimed in claim 3, wherein said condenser section condenses said vapor working fluid and creates a liquid working fluid by rejecting said heat generated from said heat generating components to a heat sink.

5. A passive cooling system as claimed in claim 4, wherein said liquid working fluid returns to said evaporator section through said second side passageway by wicking.

6. A passive cooling system as claimed in claim 2, further comprising a solar load for vaporizing said working fluid.

7. A passive cooling system as claimed in claim 5, further comprising an ultrasonic transducer for returning said working fluid to said evaporator section.

8. A passive cooling system as claimed in claim 1, further comprising a check valve located at a top o f said second side passageway for preventing reverse flow of said working fluid.

9. A passive cooling system as claimed in claim 1, wherein said integral heat pipe is a loop heat pipe.

10. A passive cooling system as claimed in claim 1, further comprising a fin located on said evaporator section and said condenser section for increased rate of thermal dissipation.

11. A passive cooling system as claimed in claim 1, further comprising conduits embedded in said first and second side passageways.

12. A passive cooling system for cooling heat generating components comprising:
   a storage means for housing heat generating components;
   a hollowed portion in said storage means for forming an integral heat pipe;
   a working fluid contained within said hollowed portion;
   an evaporator means located at a top of said hollowed portion for vaporizing said working fluid into a vapor working fluid;
   a condenser means located at a bottom of said hollowed portion for condensing said working fluid into a liquid working fluid;
   a first connector means for said vapor working fluid to flow down to said condenser means;
   a second connector means for said liquid working fluid to flow up to said evaporator means;
   a means for returning said liquid working fluid to said evaporator means located in said second connector means; and
   a means for preventing reverse flow located in said second connector means.

13. A passive cooling system as claimed in claim 12, wherein said means for returning said liquid working fluid to said evaporator means comprises a wick.

14. A passive cooling system as claimed in claim 12, further comprising an ultrasonic transducer for returning said liquid working fluid to said evaporator means.

15. A passive cooling system as claimed in claim 12, wherein said means for preventing back flow comprises a check valve.

16. A passive cooling system as claimed in claim 12, wherein said integral heat pipe is a loop heat pipe.

17. A passive cooling system as claimed in claim 12, further comprising a fin located on said evaporator means and said condenser means for increased rate of thermal dissipation.

18. A passive cooling system as claimed in claim 12, further comprising conduits embedded in said first connector means and said second connector means.

* * * * *